(12) United States Patent
Zisapel et al.

(10) Patent No.: US 6,566,389 B1
(45) Date of Patent: May 20, 2003

(54) THERAPEUTIC USES OF MELATONIN

(75) Inventors: Nava Zisapel, Tel Aviv (IL); Moshe Laudon, Kfar Saba (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 0 days.

(21) Appl. No.: 09/979,583

(22) PCT Filed: May 24, 2000

(86) PCT No.: PCT/IL00/00296
§ 371 (c)(1),
(2), (4) Date: Nov. 26, 2001

(87) PCT Pub. No.: WO00/72843
PCT Pub. Date: Dec. 7, 2000

(30) Foreign Application Priority Data

May 27, 1999 (IL) ................................................. 130171

(51) Int. Cl.[7] .......................... A61K 31/40; A61K 31/54
(52) U.S. Cl. ................. 514/418; 514/226.2; 514/225.5; 514/225.8; 514/437; 514/252.13; 514/327; 514/211.13; 514/233.5; 514/220; 514/258
(58) Field of Search ............................... 514/418, 226.2, 514/225.5, 225.8, 437, 252.13, 327, 211.13, 233.5, 220, 258

(56) References Cited

PUBLICATIONS

Database Medline ISSN 00207454 abstract. Sandyk, R., et al., "Magnetic fields in the treatment of Parkinson's disease," *International Journal of Neuroscience*, 63(1–2):141–150, Mar. 1992.

Abstract of Jeste et al., "Conventional vs. Newer Antipsychotics in elderly Patients," *Am. J. Geriatr Psychiatry*, 7:70–76, Feb. 1999.

*Primary Examiner*—Rebecca Cook
(74) *Attorney, Agent, or Firm*—Rothwell, Figg, Ernst & Manbeck

(57) ABSTRACT

A method for treating or preventing symptoms of tardive dyskensia comprises administering melatonin to patient exhibiting or liable to develop such symptoms. The melatonin is administered in an amount effective to ameliorate or prevent symptoms of tardive dyskensia developing in the patient.

11 Claims, No Drawings

THERAPEUTIC USES OF MELATONIN

This is a 371 of PCT UK 00/00296 filed May 24, 2000.

FIELD AND BACKGROUND OF THE INVENTION

The present invention relates to a method and pharmaceutical formulation for treating tardive dyskinesia Tardive dyskinesia (TD) is an involuntary movement disorder, which develops in a high percentage of patients who have been treated with neuroleptic drugs. A number of articles have appeared in the literature suggesting an inverse relationship between melatonin secretion and the incidence of TD symptoms. However, to the best of our knowledge, in only one instance has administration of exogenous melatonin been attempted in this connection, in which it was found that whereas treatment with haloperidol of pinealectomized rats resulted, in significantly more severe movement disorder than in unoperated control rats, subsequent administration of melatonin (4 mg, i.p.) was associated with a non-significant reduction of the severity of movements within one hour (Sabdyk, R., et al., Int. J. Neurosci., 1989, 48 (3–4): 303-8). The amount of melatonin used in this non-significant result was equivalent to more than 1000 mg for a 70 kg human, so that it is not surprising that subsequent attempts at TD therapy have avoided the use of exogenous melatonin. In U.S. Pat. No. 5,691,324 to Sandyk, R., for example, TD is one of a number of conditions, related to deficient serotonin transmission and impaired melatonin function, which is treated by administering to a patient a composition which increases serotonin neurotransmission, followed by applying a magnetic field to the brain. The entire contents of U.S. Pat. No. 5,691,324 are incorporated herein by reference.

It has now surprisingly been found, in relation to tardive dyskinesia, that exogenous melatonin produces a significant therapeutic effect in humans, at a dosage rate which is at least one order of magnitude lower (taking into account the average weight of humans in relation to laboratory animals) than that used in the report in Int. J. Neurosci., mentioned above.

SUMMARY OF THE INVENTION

In one aspect, the present invention provides a pharmaceutical formulation which comprises, in addition to at least one carrier, diluent or adjuvant, at least one neuroleptic compound in an amount effective to exert a neuroteptic effect in a patient requiring such treatment, and melatonin in an amount effective to ameliorate or prevent symptoms of tardive dyskensia developing in the patient.

In another aspect, the invention provides use of melatonin in the manufacture of a medicament for the prevention or treatment of symptoms of tardive dyskensia in a patient. The medicament preferably takes the form of a pharmaceutical formulation, which includes at least one of the following additional components (a) and (b): (a) at least one carrier, diluent or adjuvant (b) at least one neuroleptic compound in an amount effective to exert a neuroleptic effect in a patient requiring such treatment. Further in accordance with the invention, a method for preventing or treating symptoms of tardive dyskensia in a patient, comprises administering melatonin to a patient exhibiting such symptoms or liable otherwise to develop such symptoms, in an amount effective to ameliorate or prevent symptoms of tardive dyskensia developing in the patient.

DETAILED DESCRIPTION OF THE INVENTION

The medicament/pharmaceutical formulation may be administered in any convenient form, such as one adapted for oral, rectal, parenteral or transdermal administration. It may be e.g. in unit dosage form. In a particular embodiment, the melatonin is in the form of a controlled release formulation, wherein the melatonin is preferably released at a predetermined controlled rate.

The amount of melatonin presently contemplated for use in preventing or treating tardive dyskinesia will be the amount found to be effective for this purpose, presently believed to be, in the case of oral administration, more than 0.5 mg and no more than 100 mg daily, eg. 0.5–50 mg, preferably 2.5–20 mg, and for parenteral or transdermal administration, between 0.1 and 50 mg. In accordance with the invention, an effective amount of melatonin may be formulated e.g. together with an effective dosage of a neuroleptic drug. The present medicament/pharmaceutical formulation may comprise also at least one melatonin receptor modifier and/or melatonin profile modifier.

Once the concept of the present invention for treatment or prevention of TD using melatonin is known according to the present invention, no inventive skill would be required to ascertain the range of effective amounts of melatonin for the present purpose, for various routes of administration. Where the pharmaceutical formulation includes at least one neuroleptic compound, this may for example be selected from such compounds containing at least one of the following ring systems, namely, piperidine, pirperazine, morpholine, 5,6,7,8-tetrahydroindole, phenothiazine and thioxanthene Exemplary neuroleptic compounds are chlorpromazine, triflupromazine, mesoridazine, piperacetazine, thioridazine, acetophenazine, fluphenazine, perphenazine, trifluoperazine, chlorprothixene, thiothixene, haloperidol, loxapine, molindone (c.f. Table 1), and clothiapine, clozapine, olanzapine, risperidone and zuclopenthixol acetate, and their pharmaceutically acceptable salts).

TABLE 1

| | Neuroleptic Compounds | | | |
| --- | --- | --- | --- | --- |
| | Daily Dosage* | | Modes of | Intramuscular |
| Compound | possible | usual | Administration | single dosage* |
| Chlorpromazine+ | 25–2000 | 300–800 | oral; parenteral, rectal, SR | 20–50 |
| Triflupromazine+ | 25–300 | 100–150 | oral, parenteral | 20–60 |
| Mesoridazine besylate | 25–300 | 75–300 | oral, parenteral | 25 |
| Piperacetazine | 5–200 | 20–160 | oral | — |
| Thioridazine+ | 20–800 | 200–600 | oral | — |
| Acetophenazine maleate | 20–600 | 60–120 | oral | — |
| Fluphenazine+ | 0.5–30 | 1–20 | oral, parenteral | 1.25–2.5 |

TABLE 1-continued

Neuroleptic Compounds

| Compound | Daily Dosage* possible | Daily Dosage* usual | Modes of Administration | Intramuscular single dosage* |
|---|---|---|---|---|
| Perphenazine | 4–64 | 8–32 | oral, parenteral, SR | 5–10 |
| Trifluoperazine+ | 2–60 | 6–20 | oral, parenteral | 1–2 |
| Chlorprothixene | 30–600 | 50–400 | oral, parenteral | 25–50 |
| Thiothixene+ | 6–60 | 6–30 | oral, parenteral | 2–4 |
| Haloperidol | 1–100 | 6–20 | oral, parenteral | 2–5 |
| Loxapine succinate | 20–250 | 60–100 | oral, parenteral | 12.5–50 |
| Molindone+ | 12–225 | 50–100 | oral | — |

*mg + hydrochloride SR = sustained release (oral)

EXAMPLE 1

The following ingredients are mixed together and the mixture was compressed in a 7 mm cylindrical punch, at 2.5 tons, in order to make controlled release tablets: chlorpromazine hydrochloride (275 mg/tablet), melatonin (5 mg/tablet), and Eudragit™ RS 100 acrylic resin carrier (Rohm Pharma) and lactose in an approximately 1:1 ratio by weight. While this formulation should be administered in accordance with a physicians instructions, it is presently contemplated that two such tablets taken two hours before bedtime would be appropriate.

EXAMPLE 2

The following ingredients are mixed together and the mixture was compressed in a 7 mm cylindrical punch, at 2.5 tons, in order to make controlled release tablets: perphenazine (10 mg/tablet), melatonin (5 mg/tablet), and Eudragit™ RSPO acrylic resin carrier (Rohm Pharma), lactose and calcium hydrogen phosphate in an approximately 2:1:2.5 ratio by weight. While this formulation should be administered in accordance with a physicians instructions, it is presently contemplated that two such tablets taken two hours before bedtime would be appropriate.

EXAMPLE 3

The effect of melatonin on tardive dyskinesis was determined on a trial population of 22 patients, of whom 6 were schizoaffective and 16 were paranoid schizophrenics. All patients, who had been receiving long-term neuroleptic treatment, were diagnosed according to DSM IV. They consisted of 11 men and 11 women, age 39±15 years, age range 17–61 years, of whom 19 completed the trial and are included in the results. In a randomized, double blind, crossover manner, subjects were given daily either 2×5 mg melatonin in a controlled-release formulation (Circadin™, Neurim Pharmaceuticals, Israel), two hours before bedtime, or a placebo of identical appearance, for a period of six weeks, with a four week placebo wash-out between two treatment periods. Besides the melatonin or placebo, each patient received, respectively, one of the following daily doses (mg) of neuroleptic, or in two cases no neuroleptic drug: chlorpromazine (250), clothiapine (20, 80 or 160), clozapine (200, 400 or 550), haloperidol (5, 15 or 20), olanzapine (10 or 15), perphenazine (4, 8, 12, 32 or 32), risperidone (4) or zuclopenthixol acetate (4 or 20). During the last week of each treatment period, TD severity was assessed using the Abnormal Involuntary Movements Scale (AIMS) and comparisons were made between placebo or melatonin treatments, and baseline. The results are shown in tables 2 and 3.

TABLE 2 results of T-tests for various AIMS parameters

| AIMS sub-scale | Parameter | T-test ($t_{21}$)§ | p |
|---|---|---|---|
| 1 | facial and oral movements | −1 | 0.33 |
| 2 | lips and perioral area | −3.92 | <0.001* |
| 3 | jaw | −1.14 | 0.27 |
| 4 | tongue | −0.81 | 0.43 |
| 5 | arms, hands | −1.78 | 0.09 |
| 6 | legs, knees | −2.81 | 0.01* |
| 7 | neck, shoulder | −2.49 | 0.02* |
| 8 | severity of abnormal movements | −1.82 | 0.08 |
| 9 | implication due to abnormal movements | −1.14 | 0.27 |
| 10 | patient's awareness | delta = 0 | |
| 11 | problem with teeth | delta = 0 | |

§comparison of the baseline/administration difference, placebo vs. melatonin
*significant outcome

TABLE 3 results of studies on the effect of melatonin on tardive dyskinesis

| AIMS sub-scale | Intensity of Movements (standard deviation) | | | |
|---|---|---|---|---|
| | baseline | placebo | baseline | melatonin |
| 1 | 2.14 (0.89) | 2.00 (0.82) | 2.18 (0.80) | 1.91 (0.87) |
| 2 | 3.27 (0.70) | 3.27 (0.70) | 3.50 (0.74) | 3.00 (0.98) |
| 3 | 3.00 (1.07) | 2.73 (1.12) | 3.09 (1.11) | 2.68 (1.13) |
| 4 | 3.55 (0.67) | 3.32 (0.65) | 3.50 (0.67) | 3.18 (0.80) |
| 5 | 1.73 (0.83) | 1.64 (0.79) | 1.91 (0.92) | 1.50 (0.74) |
| 6 | 1.23 (0.53) | 1.23 (0.53) | 1.55 (0.91) | 1.27 (0.63) |
| 7 | 1.18 (0.50) | 1.14 (0.47) | 1.55 (1.06) | 1.27 (0.70) |
| 8 | 3.36 (0.73) | 3.27 (0.70) | 3.50 (0.74) | 3.27 (0.88) |
| 9 | 3.09 (0.81) | 2.95 (0.79) | 3.00 (0.87) | 2.73 (0.88) |
| 10 | 1.73 (0.70) | 1.73 (0.70) | 1.73 (0.70) | 1.73 (0.70) |
| 11 | 1.91 (0.29) | 1.91 (0.29) | 1.91 (0.29) | 1.91 (0.29) |

Conclusion. The present study revealed a highly significant ($p<0.0001$, MANOVA) decrease, ie. improvement, after melatonin administration compared with placebo (−3±2.1 and −1±1.3, respectively).

While the present invention has been particularly described with reference to certain embodiments, it will be apparent to those skilled in the art that many modifications and variations may be made. The invention is accordingly not to be construed as limited in any way by such embodiments, rather its concept is to be understood according to the spirit and scope of the claims which follow.

What is claimed is:

1. A pharmaceutical formulation which comprises, in addition to at least one carrier, diluent or adjuvant, at least one neuroleptic compound in an amount effective to exert a neuroleptic effect in a patient requiring said treatment, and melatonin in an amount effective to ameliorate or prevent symptoms of tardive dyskensia developing in the patient.

2. The pharmaceutical formulation according to claim 1, which further comprises at least one of the following features:
   (i) it is adapted for oral, rectal, parenteral or transdermal administration;
   (ii) it is in unit dosage form, each unit dosage form comprising an amount of melatonin which lies within the range of 2.5–20 mg; or
   (iii) it is in the form of a controlled release formulation, wherein the melatonin is preferably released at a predetermined controlled rate.

3. The pharmaceutical formulation of claim 1 which further comprises at least one melatonin receptor modifier or melatonin profile modifier.

4. The pharmaceutical formulation of claim 1 wherein said neuroleptic compound is selected from the compounds containing at least one of the following ring systems: piperidine, piperazine, morpholine, 5,6,7,8-tetrahydroindole, phenothiazine or thioxanthene.

5. The pharmaceutical formulation according to claim 1, 2, 3 or 4 wherein said neuroleptic compound is selected from chlorpromazine, triflupromazine, mesoridazine, piperacetazine, thioridazine, acetophenazine, fluphenazine, perphenazine, trifluoperazine, chlorprothixene, thiothixene, haloperidol, loxapine, molindone, clothiapine, clozapine, olanzapine, risperidone, and zuclopenthixol acetate, or a pharmaceutically acceptable salt thereof.

6. A method for the prevention or treatment of symptoms of tardive dyskensia in a patient, which comprises administering melatonin to a patient exhibiting said symptoms or liable to develop said symptoms, in an amount effective to ameliorate or prevent symptoms of tardive dyskensia developing in the patient.

7. A method for the prevention or treatment of symptoms of tardive dyskensia in a patient, which comprises administering to a patient exhibiting said symptoms or liable to develop said symptoms a pharmaceutical formulation comprising at least one neuroleptic compound and melatonin, wherein said neuroleptic compound is administered in an amount effective to exert a neuroleptic effect in said patient and said melatonin is administered in an amount effective to ameliorate or prevent symptoms of tardive dyskensia developing in the patient.

8. The method according to claim 7, wherein said pharmaceutical formulation further comprises at least one of the following features:
   (i) it is adapted for oral, rectal, parenteral or transdermal administration;
   (ii) it is in unit dosage form, each unit dosage form comprising an amount of melatonin which lies within the range of 2.5–20 mg; or
   (iii) it is in the form of a controlled release formulation, wherein the melatonin is preferably released at a predetermined controlled rate.

9. The method according to claim 7 or 8, wherein said formulation further comprises at least one melatonin receptor modifier or melatonin profile modifier.

10. The method according to claim 7 or 8, wherein said neuroleptic compound is selected from the compounds containing at least one of the following rings systems, piperidine, piperazine, morpholine, 5,6,7,8-tetrahydroindole, phenothiazine or thioxanthene.

11. The method according to claim 7 or 8, wherein said neuroleptic compound is selected from chlorpromazine, triflupromazine, mesoridazine, piperacetazine, thioridazine, acetophenazine, fluphenazine, perphenazine, trifluoperazine, chlorprothixene, thiothixene, haloperidol, loxapine, molindone, clothiapine, clozapine, olanzapine, risperidone and zuclopenthixol, or a pharmaceutically acceptable salt thereof.

* * * * *